US011925340B2

(12) United States Patent
Whitman

(10) Patent No.: US 11,925,340 B2
(45) Date of Patent: *Mar. 12, 2024

(54) LIGHTED POLYHEDRAL RETRACTOR

(71) Applicant: Atlantic Health System, Inc., Morristown, NJ (US)

(72) Inventor: Eric D. Whitman, Mountain Lakes, NJ (US)

(73) Assignee: Atlantic Health System, Inc., Morristown, NJ (US)

( * ) Notice: Subject to any disclaimer, the term of this patent is extended or adjusted under 35 U.S.C. 154(b) by 814 days.

This patent is subject to a terminal disclaimer.

(21) Appl. No.: 16/925,987

(22) Filed: Jul. 10, 2020

(65) Prior Publication Data

US 2020/0337687 A1    Oct. 29, 2020

Related U.S. Application Data

(63) Continuation of application No. 16/154,700, filed on Oct. 8, 2018, now Pat. No. 10,758,218, which is a (Continued)

(51) Int. Cl.
*A61B 17/02* (2006.01)
*A61B 17/00* (2006.01)
(Continued)

(52) U.S. Cl.
CPC ............. *A61B 17/02* (2013.01); *A61B 90/30* (2016.02); *A61B 90/57* (2016.02); *A61B 2017/00876* (2013.01); *A61B 2090/309* (2016.02)

(58) Field of Classification Search
CPC ......... A61B 17/02; A61B 90/30; A61B 90/57; A61B 2090/309; A61B 2017/00876; A61B 17/0281; A61B 1/32; A61B 34/70
See application file for complete search history.

(56) References Cited

U.S. PATENT DOCUMENTS 3,667,474 A * 6/1972 Lapkin .................. A61M 29/02
606/198
5,681,349 A * 10/1997 Sugarbaker ............ A61B 17/29
606/151
(Continued)

*Primary Examiner* — Kevin T Truong
*Assistant Examiner* — Diana Jones
(74) *Attorney, Agent, or Firm* — McHattie Law Firm; Jon Tyler

(57) ABSTRACT

A surgical retractor includes a structure including a plurality of legs and a plurality of joints, each leg being connected to at least one second leg at a joint. The structure has a non-expanded state, and an expanded state in which the structure forms a three dimensional structure having an internal volume. The structure has first and second manipulator arms, each of the manipulator arms being connected to at least two joints of the structure. The manipulator arms may be manipulated by a hand of a user. The retractor also includes a connector that holds the first and second manipulator arms in a crossed position. The connector holds the first and second manipulator arms at a point of intersection. The connector allows a user to move the manipulator arms and cause an angle formed by the manipulator arms to change. Movement of the first and second manipulator arms causes the structure to move between the non-expanded state and the expanded state.

12 Claims, 17 Drawing Sheets

Related U.S. Application Data continuation-in-part of application No. 14/791,095, filed on Jul. 2, 2015, now Pat. No. 10,123,791.

(51) Int. Cl.
*A61B 90/30* (2016.01)
*A61B 90/57* (2016.01)

(56) References Cited

U.S. PATENT DOCUMENTS

| | | | | |
|---|---|---|---|---|
| 5,755,661 | A * | 5/1998 | Schwartzman | A61B 17/0281 600/210 |
| 5,761,871 | A * | 6/1998 | Atake | E04B 1/3441 52/645 |
| 2003/0176883 | A1* | 9/2003 | Sauer | A61B 17/0218 606/198 |
| 2008/0045803 | A1* | 2/2008 | Williams | A61B 1/00052 600/204 |
| 2014/0114331 | A1* | 4/2014 | Levin | A61F 2/0063 606/151 |

* cited by examiner

LIGHTED POLYHEDRAL RETRACTOR

LIGHTED POLYHEDRAL RETRACTOR

LIGHTED POLYHEDRAL RETRACTOR

LIGHTED POLYHEDRAL RETRACTOR

LIGHTED POLYHEDRAL RETRACTOR

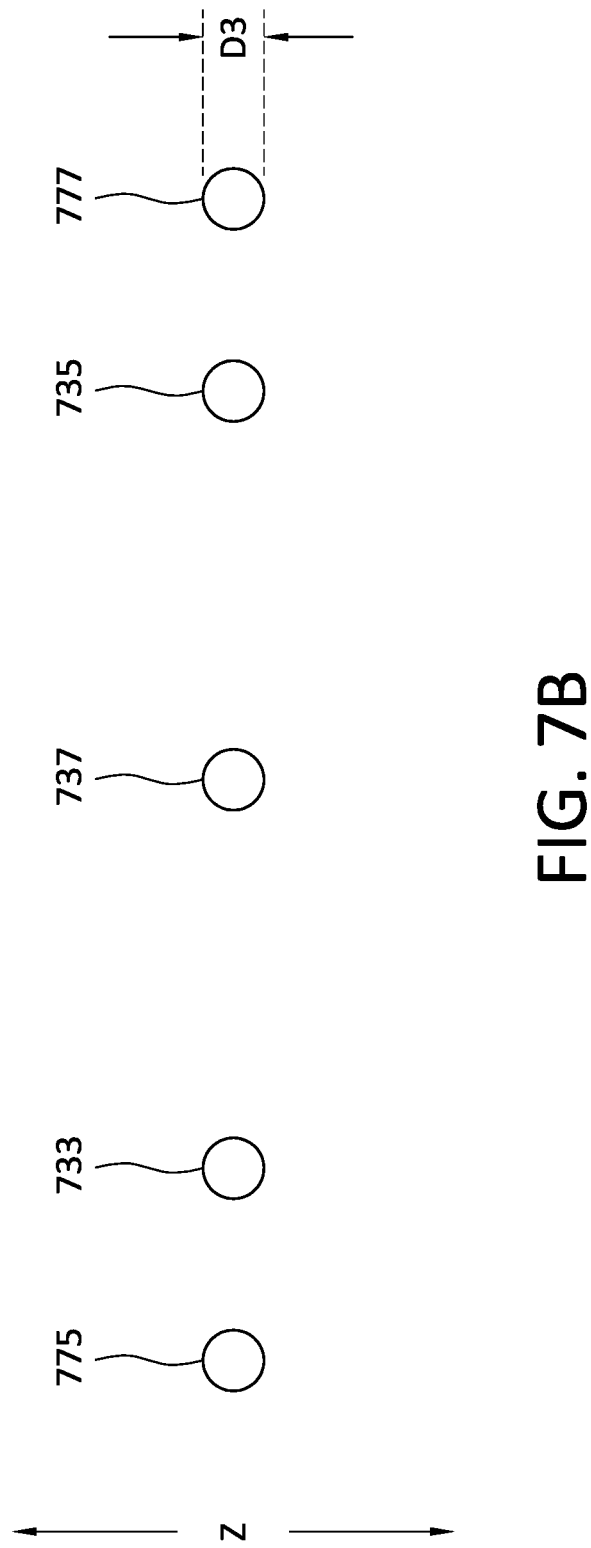

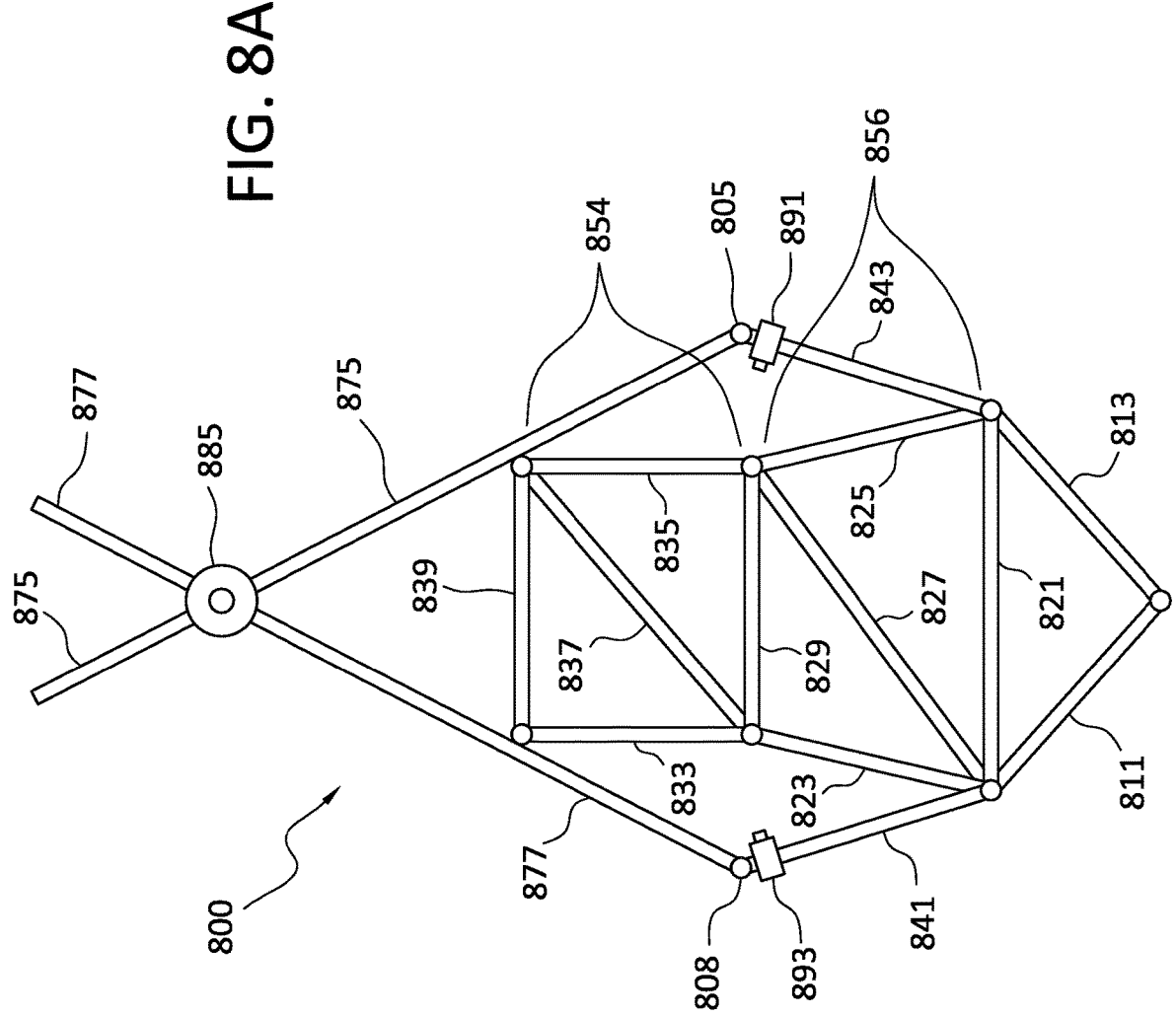

LIGHTED POLYHEDRAL RETRACTOR

This application is a continuation of U.S. patent application Ser. No. 16/154,700 filed Oct. 8, 2018, which is a continuation-in-part U.S. patent application Ser. No. 14/791,095 filed Jul. 2, 2015, each of which is incorporated by reference herein in its entirety and for all purposes.

FIELD OF THE INVENTION

The present invention provides a surgical retractor that provides improved access to a surgical space, devised in the shape of a partial polyhedron, and also provides improved visualization of the surgical space with light emitting elements placed within the structure.

Typically, surgical retractors 'retract' something, that is, pull something 'open' along generally an "x" and "y" axis so that the user can see and have access to what is underneath. Surgical retraction is generally targeted to a specific tissue or a specific point. What has not heretofore been satisfactorily accomplished is expansion of a general work area around the area of interest, for example, not just limited to an "x" and "y" axis retraction, but even expansion of a general area along a plurality of axes. While that concept may not be possible in some surgical circumstances, it may be very desirable and possible in many instances. Specifically, it may be desirable to have a retractor that does not just merely retract one specific tissue or point of interest but is capable of expanding a work area of interest in multiple dimensions in multiple ways creating the most suitable work environment possible. The instant invention accomplishes just that and provides an evenly illuminated environment also.

BACKGROUND

Surgical retractors are known. Surgical retractors that expand in place are known. For example, U.S. Pat. No. 8,075,582 discloses an expandable intra-gastric balloon (1) for treating obesity, the balloon being for implanting in the stomach in order to reduce its volume, said balloon (1) comprising a first flexible pouch (2) provided with first connection means (3) for receiving a connection member (6) that is for connection to a first fluid source in order to expand said first pouch (2) in the stomach by filling it with fluid, the balloon being characterized in that it includes at least one second flexible pouch (20) provided with second connection means (3), said second connection means (3) being separate from the first connection means (3) in such a manner as to be capable of being connected to a second fluid source different from the first fluid source. The invention applies to treating obesity.

In another example, U.S. Pat. No. 7,625,339 discloses a blade extending tower for setting blade depth on retractors having telescoping or extending blades. The blade extending tower features a base, a column extending from the base, and mating features on the column configured to engage the blades of a retractor to extend the blades to a desired blade depth. Blade depth of the retractor is set by sliding the retractor onto the blade extending tower such that the mating features of the blade extending tower engage the blades or the retractor, stopping the blades' progression while the rest of the retractor continues along the length of the column. Thus, the blades of the retractor are extended from the retractor to a depth determined by the configuration of the blade extending tower.

In another example, U.S. Pat. No. 5,402,772 discloses an apparatus for retracting an organ inside the body to gain access to an adjacent tissue. The apparatus comprises an expandable cage and an expansion element. The expandable cage is capable of being inserted into the body through a small incision or puncture in a collapsed state. The expansion element is for selectively expanding the expansible cage inside the body to an expanded state. The expansion element includes an envelope enclosing a fluid-inflatable chamber. The expansible cage includes an additional envelope mounted inside the inflatable chamber and enclosing an additional fluid-inflatable chamber. The expansible cage is additionally capable of maintaining the expanded state independently of the expansion element after the expansible cage has been expanded by the expansion element to the expanded state.

In another example, U.S. Patent Application US2004/0236186 discloses an expandable surgical retractor for use in minimal incision surgery. The retractor consists of a fiber optic central rod surrounded by flexible wires designed to create an open space for visualization and surgical work within an illuminated surgical field. The flexible wires are disposed via selective pressure of the surgeon and are variable in number. The configuration will allow for both forward and back illumination of the surgical field. The expandable surgical retractor allows for surgical visualization in anatomical areas heretofore too complicated for surgical consideration. Other embodiments of the expandable surgical retractor are contemplated wherein a handle with an aperture may replace the central rod. The flexible wires may fit in openings around the aperture. The handle, in this embodiment, may have a light source and may be adapted to be used in select areas of anatomy. Further, the handle may be transparent. Thus, incorporating light sources into an expandable retractor are known.

In another example, U.S. Pat. No. 7,909,761 discloses methods and apparatus for a surgical retractor include a ring, a plurality of flexible straps connected to the ring, a patch of hook or loop material connected to each strap, a coordinating patch of hook or loop material connectable to the patient's skin or the surgical drape. The flexible straps of the surgical retractor may be frangibly connected together. LEDs molded into the distal end create a light source to illuminate the surgical site. The ring may take several forms including a flexible or adjustable ring and an inflatable bladder. The ring of the surgical retractor is inserted into the surgical incision, a patch of loop fastener is attached to the patient, a set of straps connected to the ring are pulled outward and the hook portion is applied to the loop portion to hold the incision open. The retractor is useable for thoracic and other types of surgery.

Many types of lights sources integrated with various retractor types are known. For example, U.S. Pat. No. 7,922,658 discloses a blade for a surgical retractor. The blade includes a base portion and a distal portion. The base portion may be attached to a frame of a surgical retractor. The distal portion may be removably coupled to the base portion and may be unitarily constructed of a translucent material. A light source may be removably coupled to the distal portion. The distal portion may be disposable.

In another example, U.S. Pat. No. 7,556,601 discloses methods and devices for illuminating a surgical space during surgery in a patient are provided. A retractor provides a working path for access to a location in the patient. A light instrument is positionable in working channel to emit light at the surgical space without substantially obstructing access to the surgical space.

In another example, U.S. Patent Application US2003/0095781 discloses illuminated surgical retractors include at least one retractor blade and a light delivery system. In some embodiments of the invention, the light delivery system includes a light emitter in the form of an elongated light emitting blade portion extending along the length of the retractor blade. The light emitter may be coupled to a light source integral with the retractor for illuminating all or a portion of the length of the light emitter or retractor blade. In other embodiments of the invention, the light delivery system may include an array of lights which may be attached directly to the retractor blade or to a support in the shape of an elongated blade that extends along the length of the retractor blade for illuminating all or a portion of the length of the retractor blade.

Therefore, there remains an unmet need for the device of the invention of the present application that provides improved unobstructed free and direct access to an evenly dimensioned surgical area with full geometrically even illumination providing the surgeon heretofore unfettered views and access to critical surgical environments.

SUMMARY OF THE INVENTION

The present invention provides a surgical retractor that provides improved access to a surgical space. Specifically, the instant invention provides a surgical retractor that is devised in the shape of a partial polyhedron, mechanically implemented by placing at a designated area and then expanding along one or more of its partial polyhedral axes to uniformly retract the designated body tissues and expand the accessible surgical space while also providing improved visualization of the surgical field with strategically placed light emitting elements at specific locations along the partial polyhedral framework.

In accordance with an embodiment, a surgical retractor device includes a structure comprising a plurality of legs and a plurality of joints, each leg being connected to at least one second leg at a joint, wherein the structure has a non-expanded state in which the structure does not form an internal three-dimensional volume and an expanded state in which the structure forms a three-dimensional structure having an internal volume. The retractor also includes first and second manipulator arms. Each of the first and second manipulator arms is connected to at least two joints of the structure. The manipulator arms are adapted to be manipulated by a hand of a user. The retractor also includes a connector adapted to hold the first and second manipulator arms in a crossed position, defining a point of intersection of the first and second manipulator arms. The connector holds the first and second manipulator arms at the point of intersection and is adapted to allow the first and second manipulator arms to move to cause an angle formed by the first and second manipulator arms to change in response to pressure provided by the hand of the user. Movement of the first and second manipulator arms causes the structure to move between the non-expanded state and the expanded state.

In one embodiment, the legs, manipulator arms, and joints may be formed of plastic, ceramic, or metal, or a combination of materials.

In another embodiment, the retractor device includes a plurality of lighting elements, each lighting element being connected to a selected one of the plurality of legs. Each lighting element may be a light emitting diode light source, for example.

In another embodiment, the plurality of legs form a rectangular structure and a trapezoidal structure. When the structure is in the non-expanded state, the first and second manipulator arms, the rectangular structure, and the trapezoidal structure are positioned in the same plane. When the structure is in the expanded state, the first and second manipulator arms define a first plane, the rectangular structure defines a second plane different from the first plane, and the trapezoidal structure defines a third plane different from the first and second planes. The first, second, and third planes define an internal three-dimensional volume that may be used as a surgical space.

In another embodiment, the plurality of legs form a first rectangular structure and a second rectangular structure. The first and second manipulator arms, the first rectangular structure, and the second rectangular structure are positioned in the same plane, when the structure is in the non-expanded state. The first and second manipulator arms define a first plane, the first rectangular structure defines a second plane different from the first plane, and the second rectangular structure defines a third plane different from the first and second planes, when the structure is in the expanded state.

In another embodiment, the connector includes a first disk comprising a channel adapted to hold the first manipulator arm, and a second disk adapted to hold the second manipulator arm, the second disk being connected to the first disk. The first and second disks are adapted to rotate relative to each other.

In another embodiment, the connector further includes a locking button having a locked position and an unlocked position, the locking button being adapted to lock the first disk in a position relative to the second disk, wherein the first and second disks can rotate relative to each other when the locking button is in the unlocked position, wherein the first and second disks cannot rotate relative to each other when the locking button is in the locked position.

In another embodiment, each of the joints includes a ball joint or a swivel.

BRIEF DESCRIPTION OF THE DRAWINGS

FIG. 7B shows a cross-section of the retractor device of FIG. 7A.

FIG. 8A shows a retractor device in a non-expanded state in accordance with another embodiment.

DETAILED DESCRIPTION

For clarity of disclosure, and not by way of limitation, the detailed description of the invention is divided into the following subsections that describe or illustrate certain features, embodiments or applications of the present invention.

Definitions

A "surgical retractor" as used herein refers to an instrument for retaining the edges of a surgical incision or organ or other tissue to allow access to a desired area for a surgical procedure.

A "light-emitting element" or "lighting element" as used herein refers to any suitable device for providing illumination directly or indirectly to the surgical space.

The Device of the Present Invention

In one embodiment the present invention provides a surgical retractor:
1. comprising a structure formed with legs that upon deployment, expand into a partial polyhedral shape;
11. said structure being compact in its non-deployed state and upon deployment, unfolds its legs to expand allowing for said deployment to simultaneously and in a plurality of directions retract a specific body tissue area;
111. said deployment initiated and controlled by the user.

In one embodiment, the surgical retractor of the present invention will also contain light emitting elements.

In one embodiment, the partial polyhedral shape is a partial icosahedron.

Figure 1:
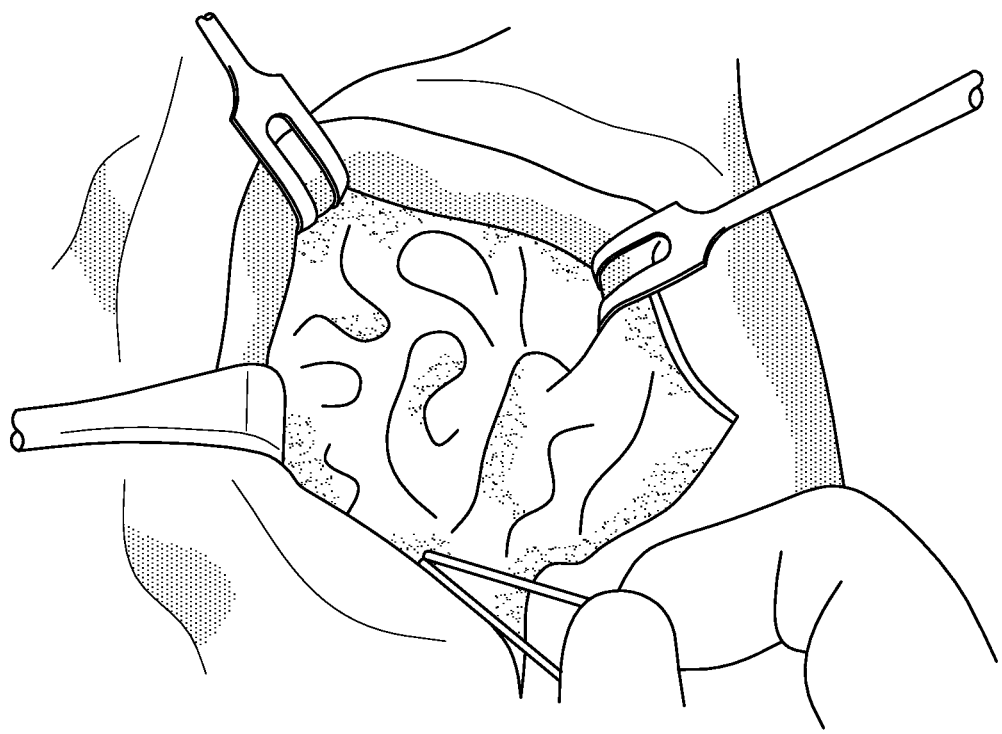
FIG. 1 shows a conventional surgical space created by the use of traditional surgical instruments restraining surface tissues in a single direction to expose underlying tissues.
Figure 2:
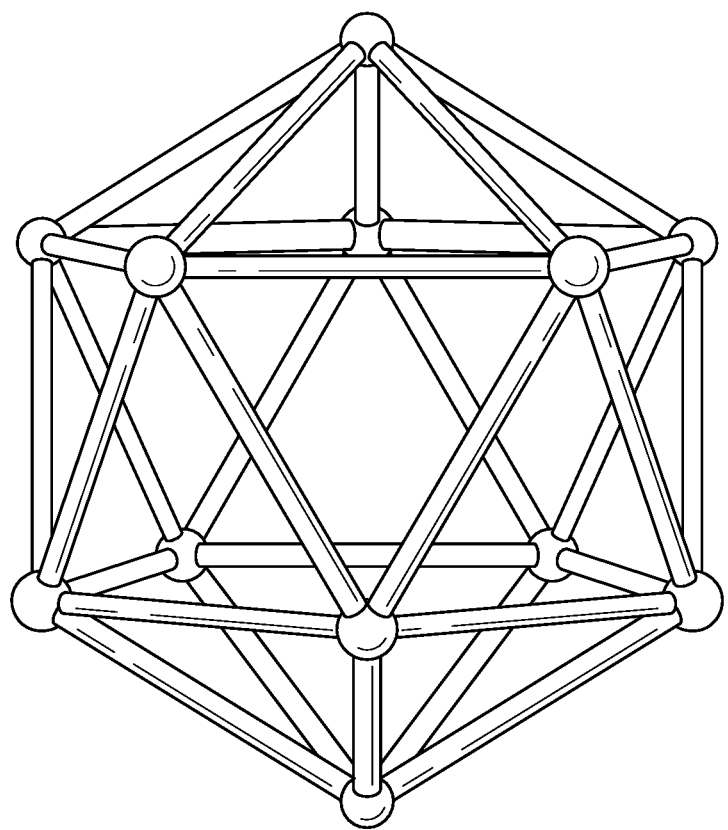
FIG. 2 shows a basic polyhedral structure further depicting how lighting elements could be placed at points along the polyhedral framework.
Figure 3:
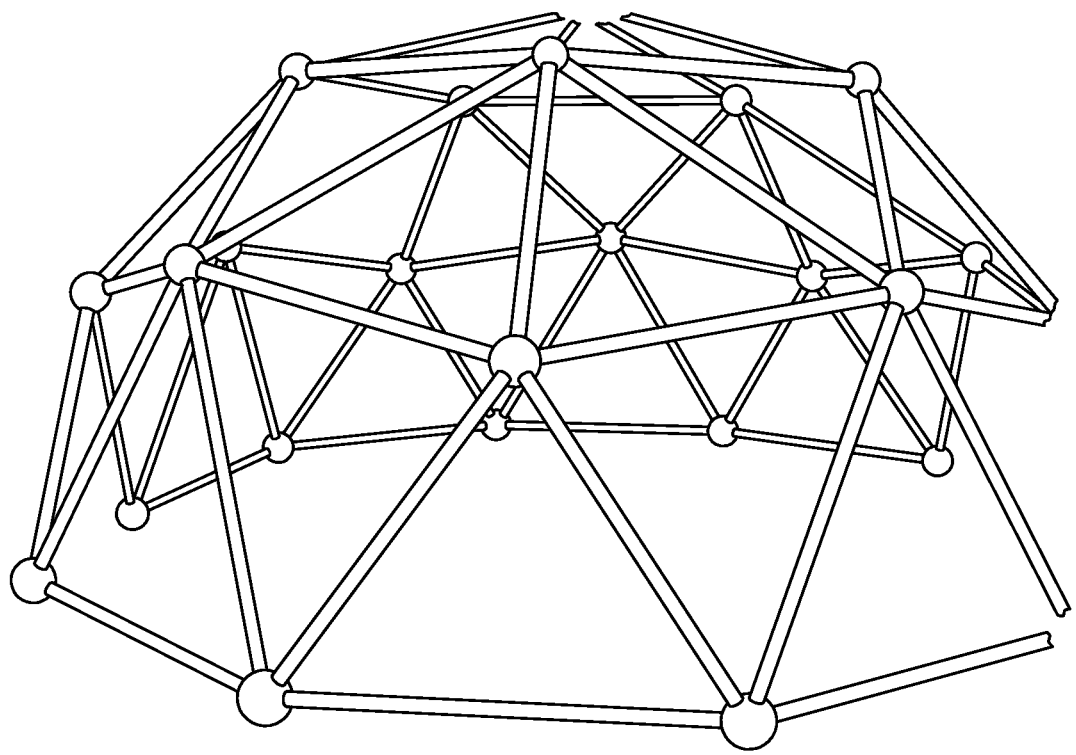
FIG. 3 shows how a polyhedral structure can be partially implemented to create/expand a defined space.
Figure 4:
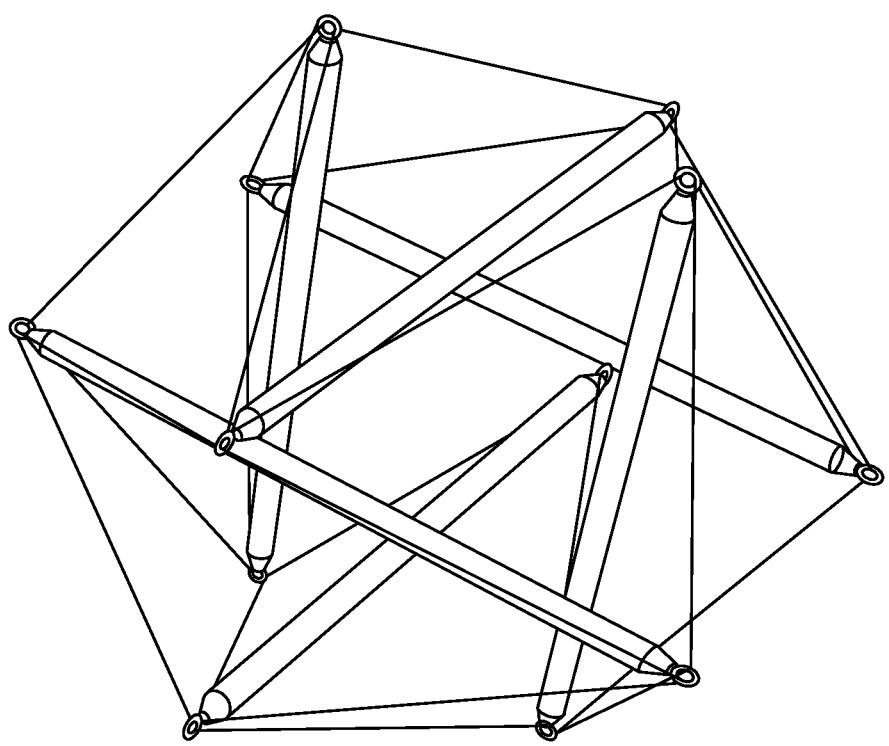
FIG. 4 shows one manner of implementing the folding and unfolding of the legs that form a polyhedral structure through the use of guide wires.

In one embodiment, the deployment of the retractor of the present invention is achieved substantially by the method disclosed in FIG. 4.

Figure 5:
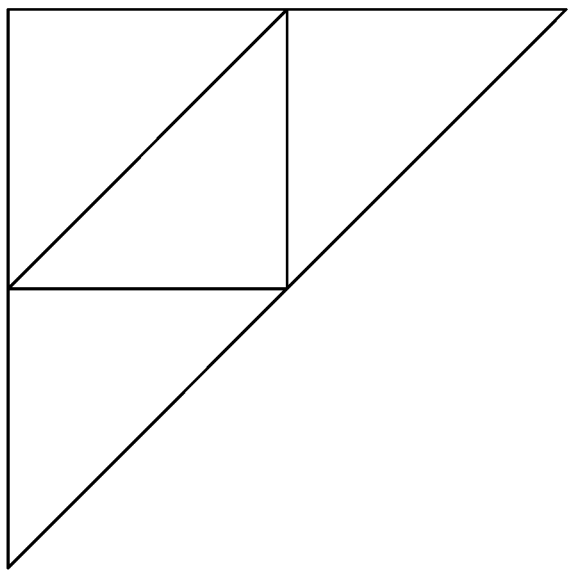
FIG. 5 shows and alternative manner of implementing the folding and unfolding of the legs that form a polyhedral structure through the use of hinged axes.
Figure 5:
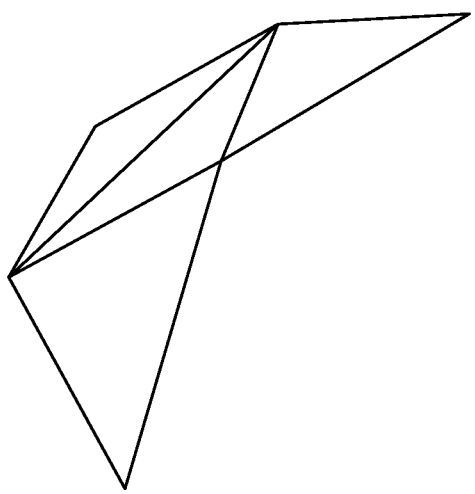

In one embodiment, the deployment of the retractor of the present invention is achieved substantially by the method disclosed in FIG. 5.

In one embodiment, the deployment of the retractor of the present invention is achieved substantially by a combination of the methods disclosed in FIGS. 4 and 5.

In one embodiment, the deployment of the retractor of the present invention is achieved by methods known by those skilled in the art.

In one embodiment, the legs of the device of the present invention are made from surgical grade steel.

In one embodiment, the legs of the device of the present invention are made from surgical grade materials other than steel, including but not limited to ceramics and plastics.

In one embodiment, the legs of the device of the present invention are hollow to allow for conduit to supply energy to light emitting elements.

In one embodiment, the device of the present invention is single use.

In one embodiment, the light emitting elements are self powered.

In one embodiment, the light emitting elements are replaceable.

In one embodiment, the light emitting elements are mounted magnetically.

In one embodiment, the light emitting elements may be user arranged.

In one embodiment, once deployed, the retractor of the present invention further comprises a locking mechanism.

In one embodiment, the locking mechanism can be unlocked whereupon the retractor may be reversibly deconstructed to allow for removal from the body cavity area where deployed.

In one embodiment, once deployed, the retractor of the present invention compacts along one or more of its partial polyhedral axes by reversibly folding the legs that form the polyhedral structure.

In one embodiment, the retractor of the present invention compacts into a substantially linear shape such that said retractor could be placed and withdrawn through a laparscopic trocar and deployed robotically and usable in laparscopic and robotic surgical procedures.

Examples

For clarity of disclosure, the following examples are based on this device implemented in connection with a typical thyroid surgery. One of ordinary skill in the art will appreciate the many applications and embodiments of the device of the present invention, for example, and not by way of limitation, any surgery that is largely internal where access is difficult, surgical spaces are confined, and surrounding tissues are delicate.

Thyroid surgery requires steady retraction throughout the procedure. Typically, surgical assistants manually provide such retraction. There have been attempts at providing self-retaining retraction. For example, a retractor made from K-wire is bent in the shape of a hook with a blunted tip and placed at the area where the tissue will be retracted. A small loop is formed at the end of the shaft of the steel wire to hold a rubber band which is attached to an ordinary pair of forceps. The forceps are fixed to an immobile part of the surgical drape providing force to the K-wire hook and providing steady retraction.

Other more specifically tailored devices have been tried. For example, the MASTR™ retractor by Surgical Innovations provides a self-retaining disposable thyroid surgery retractor which is capable of retracting the platysma muscle and strap muscles and conforms to the anatomy of the neck area and provides six direction retraction.

These methods provide uneven distribution of force. Moreover, during thyroid surgery, the optimal surgical space is a moving target as different parts of the thyroid being visible during different portions of the surgery is desirable.

The thyroid gland is located at the front of the neck, surrounded by various muscles and fatty tissues. It has two lobes that are located on each side of the trachea and are joined at the center by a bridge of thyroid tissue known as the isthmus.

Scarring from thyroid surgery is extremely visible since the incision is made on the front portion of the neck. Trauma from uneven retractor force can be a source of scarring.

Attempts have been made to provide O-ring devices common in abdominal surgeries which is a device constructed of two rings connected by a plastic material such as polyurethane. An O-ring distributes force evenly around its circumference. However, where the surgical site is not ideally perfectly round, or where the surgical site is not as deep as an abdominal surgery, bunching of the plastic material may occur obstructing the surgical field.

Moreover, none of these designs provide for a direct source of light at or near the surgical field which means that the light provided to the surgical field must come from a source further away subject to obstruction.

The device of the present invention overcomes all these negative attributes and combines all of the positive attributes.

Firstly, the construction is in the shape of a partial polyhedron, i.e., may have any number of retraction loci which provides for force uniformity of a chosen degree depending on the shape of the surgical field in a given instance.

The retraction is implemented by deploying in place and expanding and locking at the desired retraction level providing even and constant retraction force.

The retraction may be reversed by unlocking the locking mechanism and reversibly contracting the legs of the device uniformly at a desired speed.

The retractor of the device of the present invention is mechanical and may be implemented with hollow legs which allows for light emitting elements to be implemented at the retraction site directly providing for an even, constant and illuminated retraction creating the optimal surgical field.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Figure 6A:
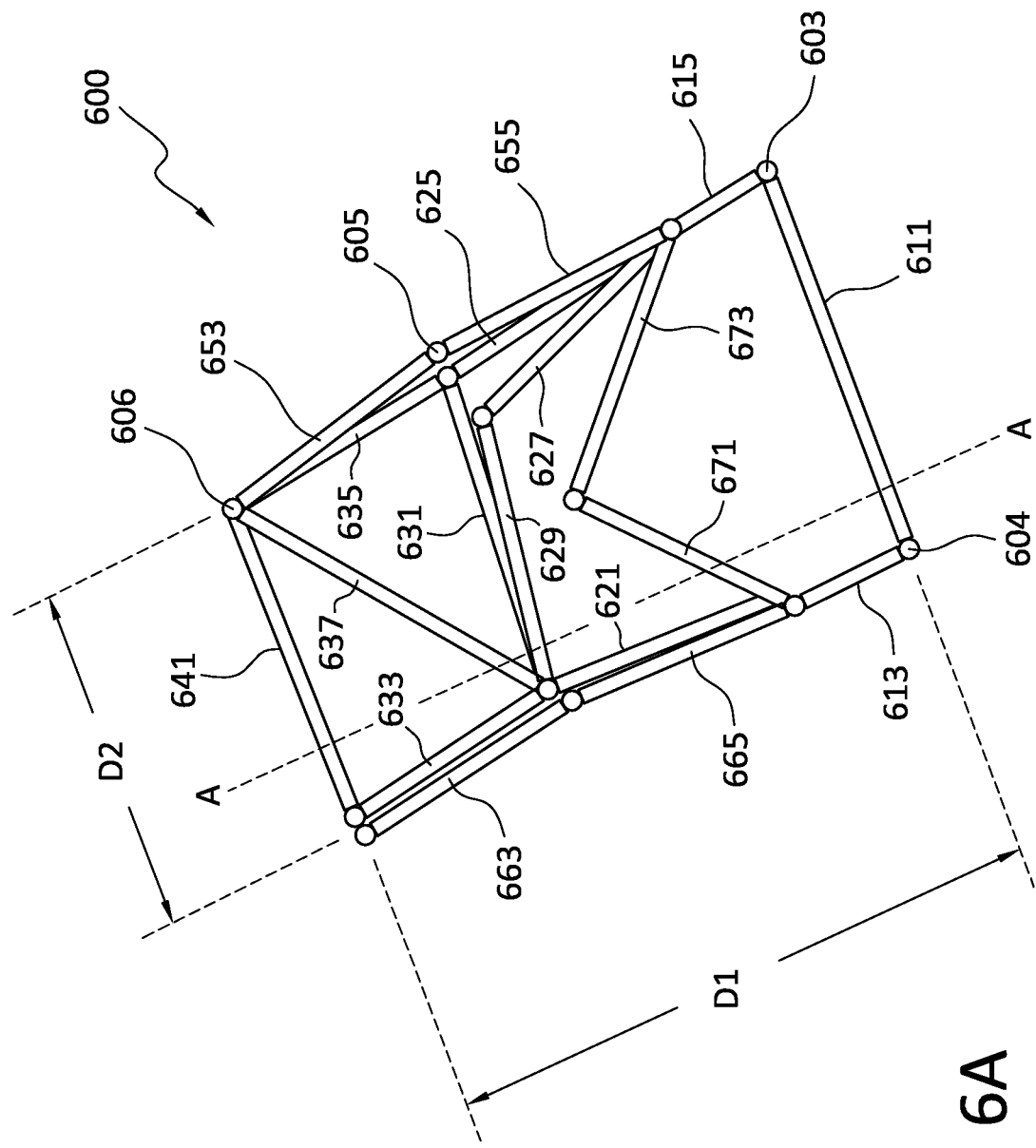
FIG. 6A shows a retractor device in a non-expanded state in accordance with an embodiment.
Figure 6B:
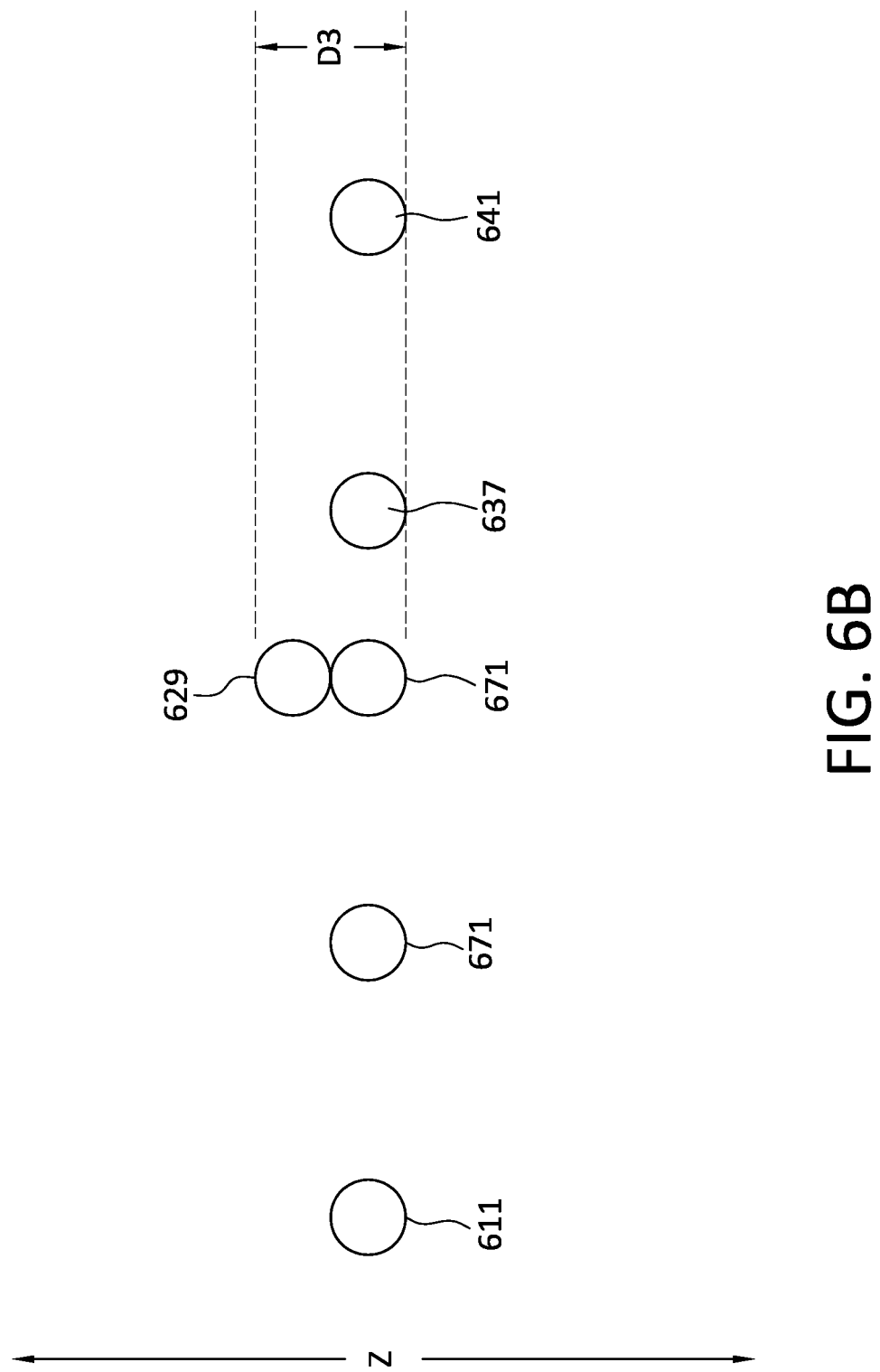
FIG. 6B shows a cross-section of the retractor device of FIG. 6A.
Figure 6C:
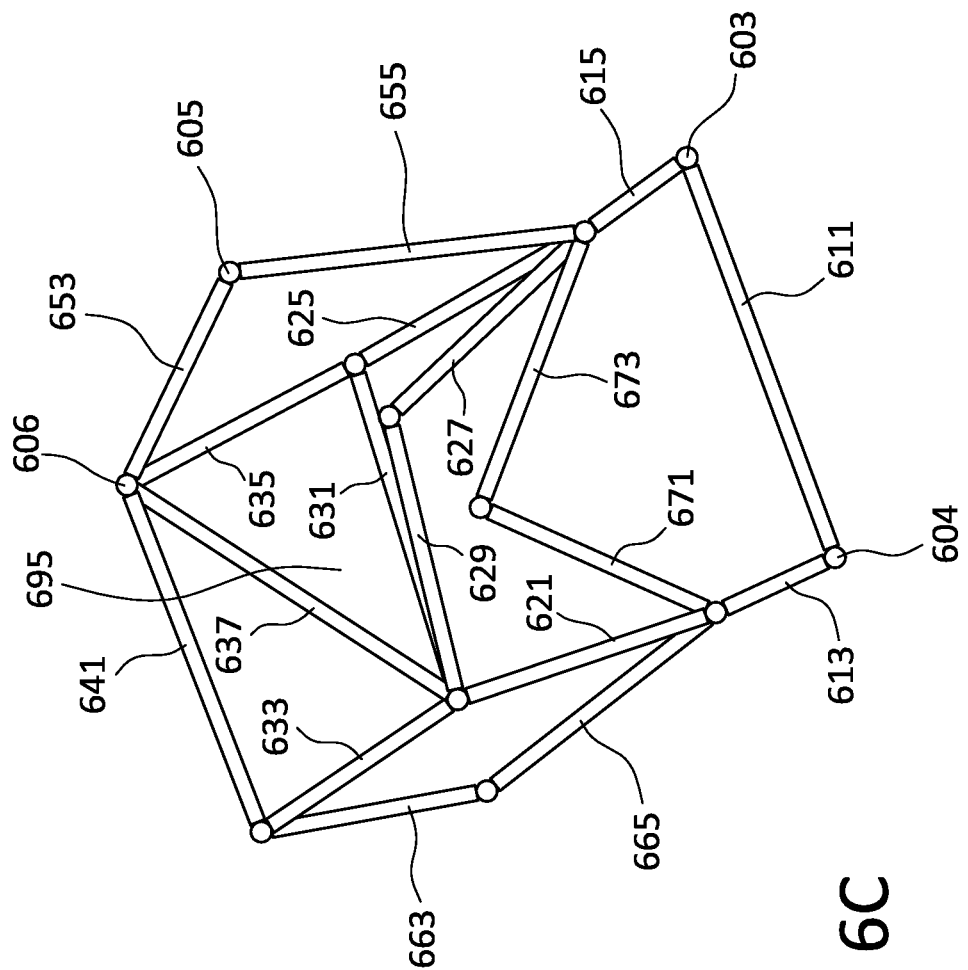
FIG. 6C shows the retractor device of FIG. 6A in an expanded state.

FIGS. 6A-6C show a retractor in accordance with another embodiment. Retractor 600 has a first, non-expanded (or flattened, or folded) configuration, shown in FIG. 6A. Retractor 600 is formed of a plurality of legs 611, 613, 615, 621, 625, 627, 629, 631, 633, 635, 637, 641, 653, 655, 663, 665, 671, and 673. In the first configuration, the legs are folded into a configuration in which the legs are arranged in a flattened configuration. In the non-expanded position, retractor 600 does not form a three-dimensional internal volume.

Each leg of retractor 600 is connected to at least one other leg at a joint. For example, in the embodiment of FIG. 6A, legs 615 and 611 are connected at joint 603. Legs 611 and 613 are connected at joint 604. Legs 655 and 653 are connected at joint 605. Legs 653 and 637 are connected at joint 606. Each joint allows two adjacent legs' positions relative to each other to be adjusted.

Each leg of retractor 600 has a length and a width (or diameter). When retractor 600 is in the flattened configuration shown in FIG. 6A, certain legs are positioned on top another leg (such as legs 629, 631); however, no leg has more than one other leg positioned above it in this way. Accordingly, retractor 600, in the folded configuration, has a first dimension DI equal to or greater than the combined lengths of legs 613, 665, and 663, and a second dimension D2 equal to or greater than the length of a leg 641. Retractor 600 has a third dimension no greater than the thickness of two legs (for example, legs 629 and 631).

FIG. 6B shows a cross-section of retractor 600 taken along line A. At various points, the retractor has a thickness, in the dimension indicated in FIG. 6B as the z-axis, equal to the thickness of one leg (e.g., the thickness of leg 611, 671, 637, or 641). Retractor 600 has a maximum thickness D3, at the point where leg 629 is folded onto and adjacent to leg 631. Therefore, the maximum thickness of retractor 600 equals twice the thickness of one leg.

FIG. 6C shows retractor 600 in a second, unfolded (or expanded) configuration in accordance with an embodiment. Legs 633, 635, 637, 641, 653, 655, 663, and 665 are raised relative to their positions shown in FIG. 6A, creating a three-dimensional volume 695 internal to the structure.

Depending on the structure of the surgical retractor, various types of joint devices may be used at each joint, depending on the degree of freedom required at the joint. For example, at certain joints, a leg may be required to be able to rotate up to 180 degrees (or more) in one or more directions. At other joints, a leg may be required to swivel up to 180 (or more) degrees in a single plane. Therefore, at selected joints a ball joint may be used. At other joints a straight pivot may be used. At other joints a gear-based joint may be used.

In one embodiment, one or more joints may include a locking mechanism. Accordingly, a user may adjust the position of one or more legs connected to a particular joint in a selected configuration and then lock the joint, fixing the legs in the selected configuration.

In some embodiments, one or more joints may include a locking ball joint.

Figure 7A:
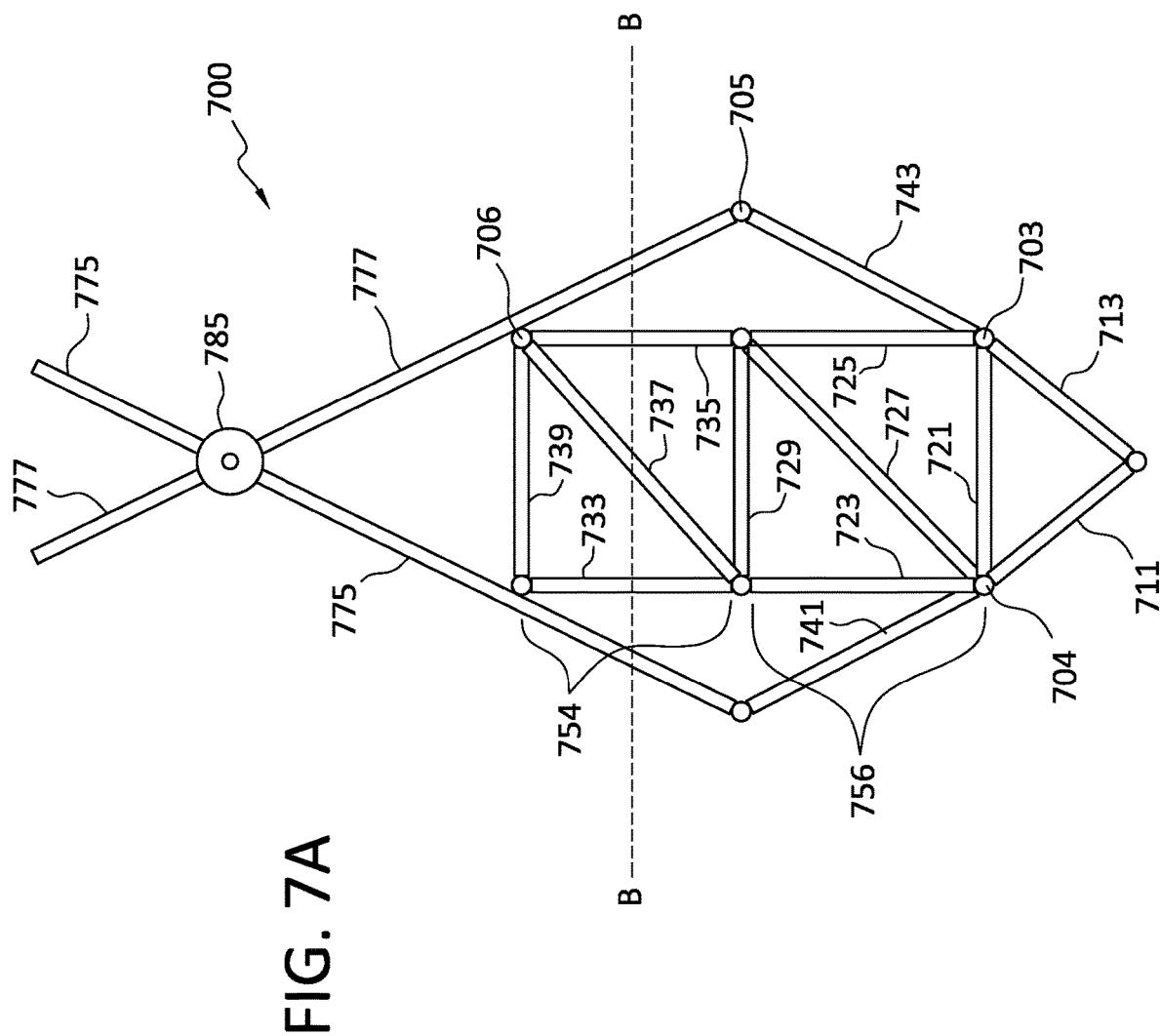
FIG. 7A shows a retractor device in a non-expanded state in accordance with another embodiment.
Figure 7C:
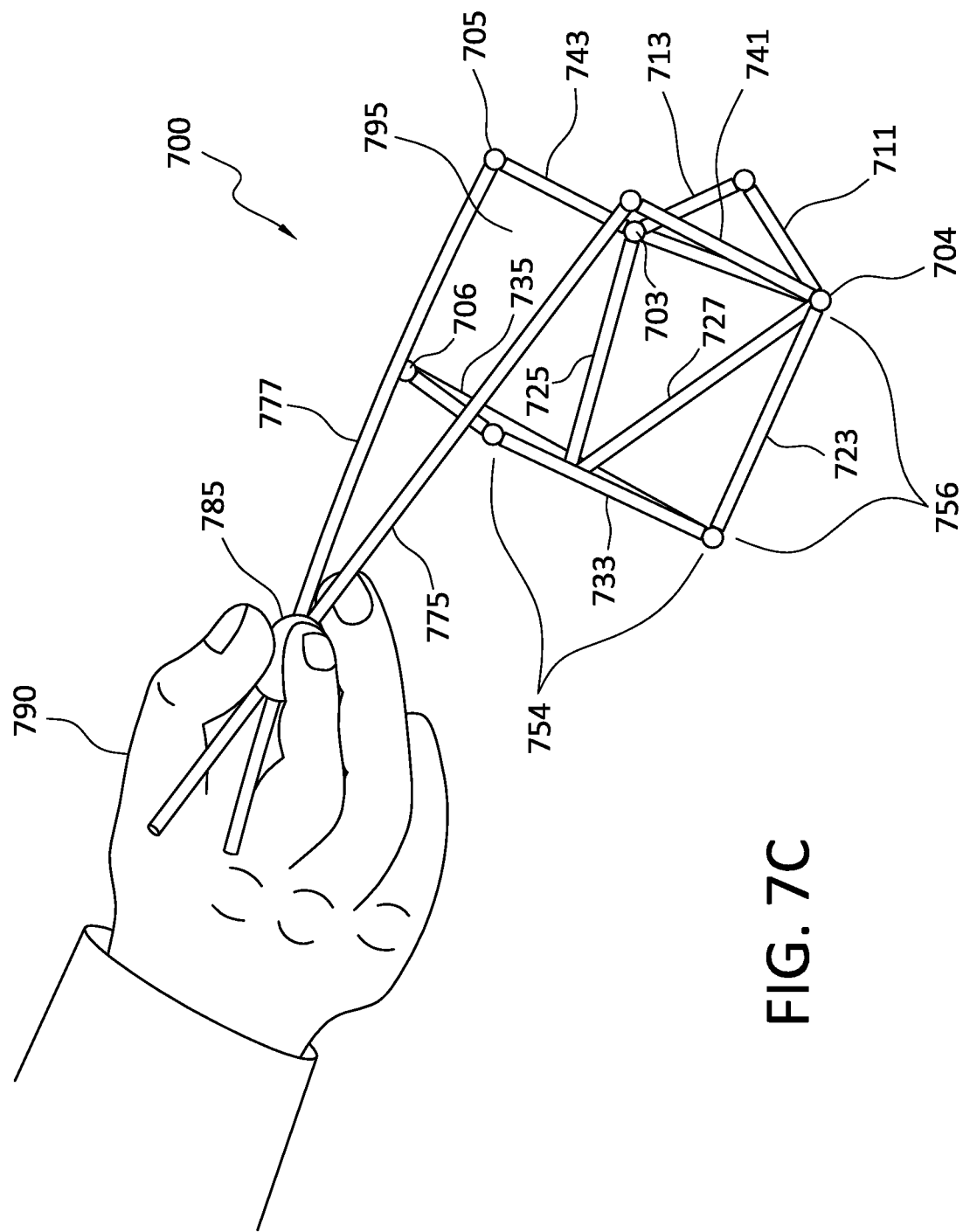
FIG. 7C shows the retractor device of FIG. 7A in an expanded state.

FIGS. 7A-7C show a retractor in accordance with another embodiment. FIG. 7A shows a retractor 700 in a folded (or flattened or non-expanded) state. Retractor 700 includes legs 711, 713, 721, 723, 725, 727, 729, 733, 735, 737, 739, 741, and 743. Retractor 700 also includes manipulator arms 775 and 777.

Retractor 700 also includes a connector 785 that holds manipulator arms 775 and 777 in a crossed position; connector 785 holds manipulator arms 775 and 777 at a point of intersection formed by the crossing of arms 775 and 775. Connector 785 includes a first channel that allows arm 775 to slide through the body of the connector and a second channel that allows arm 777 to slide through the body of the connector. By adjusting the position of connector 785 relative to the other legs of retractor 700, the positions of manipulator arms 775, 777 relative to the other legs changes.

Each leg of retractor 700 is connected to at least one other leg (or arm) at a joint. For example, in the embodiment of FIG. 7A, legs 713, 721, 725, and 743 are connected at joint 703. Legs 711, 721, 741, 723, and 727 are connected at joint 704. Leg 743 and manipulator arm 777 are connected at joint 705. Arm 777 and legs 739, 737, and 735 are connected at joint 706. Each joint allows two adjacent legs' or arms' positions relative to each other to be adjusted.

In the embodiment of FIG. 7A, legs 739, 729, and 721 are of equal length. Consequently, retractor 700 includes a first rectangular structure 754 formed by legs 739, 733, 729, and 735, and a second rectangular structure 756 formed by legs 729, 723, 721, and 725. In the non-expanded state, manipulator arms 775 and 777, rectangular structure 754 and rectangular structure 756 are positioned in a single plane, or substantially in the same plane.

FIG. 7B shows a cross-section of retractor 700 taken along line B (shown in FIG. 7A). With the exception of the thickness of connector 785, the maximum thickness D3 of retractor 700, measured in the dimension indicated in FIG. 7B as the z-axis, is equal to the thickness of one leg (e.g., the thickness of leg 775, 733, 737, 735, 777). Thus, excepting the thickness of connector 785, which is thicker than the thickness of a leg, at no point is thickness D3 of retractor 700 greater than the thickness of one leg. The thickness of the manipulator arms is the same as the thickness of the legs. Advantageously, the reduced thickness of retractor 700 when it is in the non-expanded state may allow a surgeon to more easily insert the retractor into a desired area of a patient's body (under an organ or between two organs), for example.

Referring again to FIG. 7A, connector 785 holds and secures manipulator arms 775 and 777 in a crossed position, defining a point of intersection of arms 775 and 777. However, connector 785 allows manipulator arms 775 and 777 to move such that the angle formed between the arms may be adjusted. Thus, connector 785 allows a user to manipulate arms 775 and 777 in such a way as to change the angle between arms 775 and 777. By manipulating the angle between arms 775 and 777, and the positions of arms 775 and 777 relative to the other legs of the structure, a user may cause retractor 700 to move between its non-expanded state and an expanded state.

In the expanded state, manipulator arms 775 and 777 define a first plane, rectangular structure 754 defines a second plane different from the first plane, and rectangular structure 756 defines a third plane different from the first and second planes. An internal three-dimensional volume defined by and bounded by the first, second and third planes is created.

In the illustrative example, manipulator arms 775 and 777 may be manipulated to form a three-dimensional structure such as that shown in FIG. 7C. FIG. 7C shows the retractor in an expanded state in accordance with an embodiment. Specifically, manipulator arms 775 and 777 are manipulated to cause legs 733 and 735, and legs 741 and 743, to move such that leg 741 is substantially parallel to leg 733, and leg 743 is substantially parallel to leg 735. As a result, rectangular structure 754 is substantially perpendicular to a plane formed by manipulator arms 775, 777, and rectangular structure 756 is substantially parallel to the plane formed by the manipulator arms. Thus, manipulator arms 775 and 777, rectangular structure 754, rectangular structure 756, and legs 741 and 743 form a three-dimensional box-like structure having an internal three-dimensional volume 795 between, and bounded by, legs 733, 737, 735, 741, 743, 723, 727, 725, and 721, and portions of manipulator arms 775 and 777. Advantageously, the internal volume 795 created when retractor 700 is in the expanded state may create a volume that may be used as a surgical space, for example.

Connector 785 includes first and second disks stacked concentrically one upon the other.

Figure 7D:
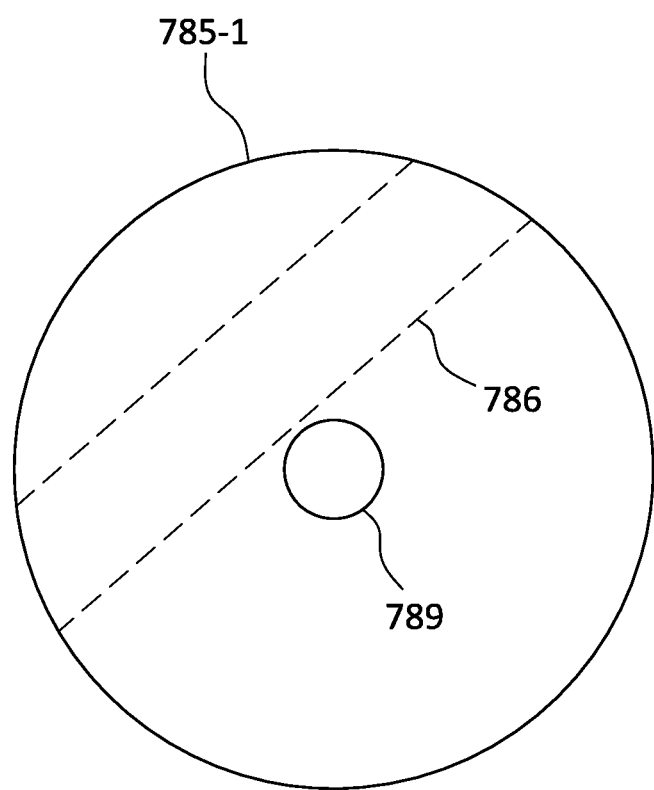
FIG. 7D shows a disk that forms part of a connector in accordance with an embodiment.

Each disk has a channel adapted to hold a manipulator arm. The disks share a common axis, and are connected along the axis, but able to rotate relative to each other. FIG. 7D shows a disk in accordance with an embodiment. Disk 785-1 is circular in shape. Disk 785-1 includes a channel 786 adapted to hold a manipulator arm. Disk 785-1 also includes a hole 789 adapted to hold a fastener, and optionally a locking mechanism. Channel 786 is off-center and thus does not pass through the geometric center of the disk.

Figure 7E:
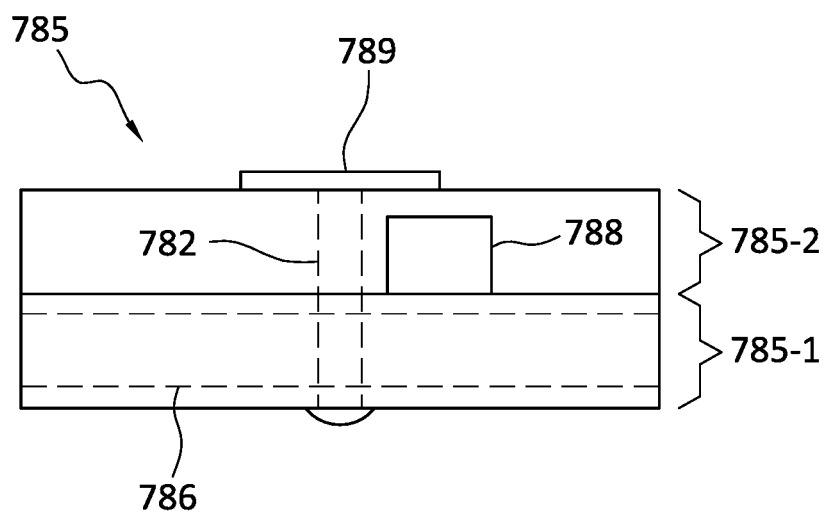
FIG. 7E shows a side view of a connector in accordance with an embodiment.

FIG. 7E shows a side view of connector 785 in accordance with an embodiment. Connector 785 includes first disk 785-1 joined concentrically to a second disk 785-2. The two disks are connected by a fastener 782. Other connecting mechanisms may be used. A locking button 789 is coupled to fastener 782. Disks 785-1, 785-2 are connected by fastener 283 but are independently able to rotate relative to each other. Disk 785-1 includes channel 786; disk 785-2 includes a channel 788. As shown in FIG. 7E, channel 788 is off-center in disk 785-2. In FIG. 7E, channel 788 is perpendicular to channel 786. However, because the disks can rotate, the angle formed by the two channels may change.

Locking button 789 is adapted to lock disks 785-1, 785-2 in a fixed position relative to each other. Locking button 789 has a locked position and an unlocked position. When locking button 789 is in the locked position, the two disks cannot rotate relative to each other. When locking button 789 is in the unlocked position, the two disks can rotate relative to each other. Therefore, a user may move the manipulator arms to desired positions forming a desired angle (while the locking button is in the unlocked position), and then press the locking button to place it in the locked position and lock disks 785-1, 785-2 in the selected position. When the locking button is locked, the angle between the manipulator arms cannot be changed.

Figure 7F:
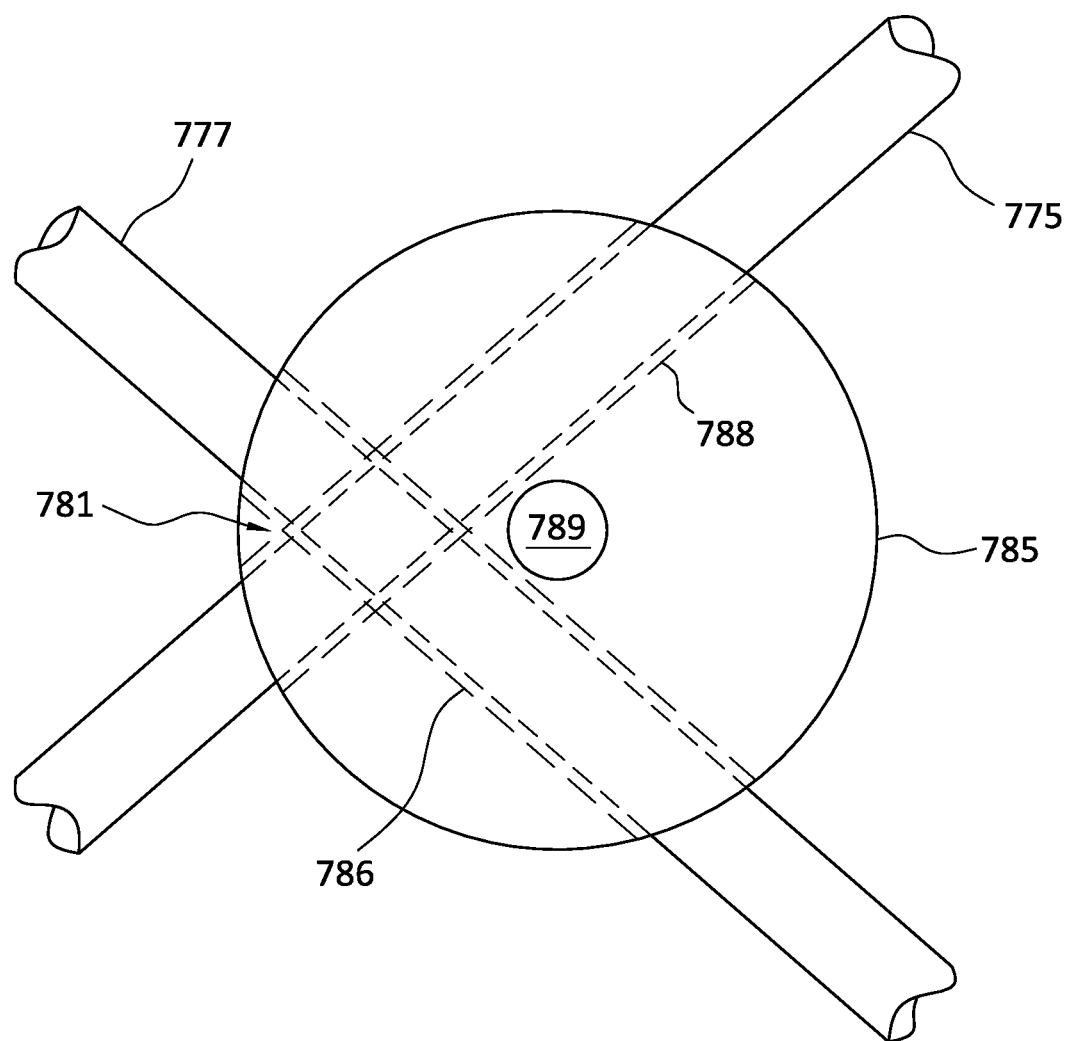
FIG. 7F shows a top view of a connector in accordance with an embodiment.

FIG. 7F shows a top view of connector 785 in accordance with an embodiment. Channels 786, 788 hold arms 777, 775, respectively, in a crossed position, defining a point of intersection 781. Because disks 785-1, 785-2 can rotate relative to each other, a user may move manipulator arms 775, 777 in a manner to change the angle formed between the manipulator arms. For example, as a user presses or pulls one or both of the manipulator arms 775, 777, the channels may rotate accordingly, allowing the user to control the angle between the manipulator arms.

The legs, arms, joints, and connector of a surgical retractor may be formed of any suitable material, such as plastic, ceramic or metal, or a combination of different materials. For example, selected components may be made of injection molded plastic. Other materials may be used.

FIG. 8A shows a surgical retractor in a non-expanded (or flattened) state, in accordance with another embodiment. Retractor 800 is similar to retractor 700 shown in FIGS. 7A-7C. Thus, surgical retractor 800 includes legs 811, 813, 821, 823, 825, 827, 829, 833, 835, 837, 839, 841, and 843, and manipulator arms 875 and 877. Surgical retractor 800 also includes a plurality of joints disposed between the legs and arms, including, for example, joints 805 and 808. Joint 805 connects leg 843 and manipulator arm 875. Joint 808 connects leg 841 and manipulator arm 877. Retractor 800 also includes a connector 885 that holds manipulator arms 875 and 877.

Retractor 800 differs from retractor 700 in that legs 829 and 839 are of equal length while leg 821 is longer than leg 829. Consequently, retractor 800 includes a first, rectangular structure defined by legs 839, 833, 829, and 835, and a second, trapezoidal structure formed by legs 829, 823, 821, and 825. In the non-expanded state, manipulator arms 875, 877, rectangular structure 854, and trapezoidal structure 856 are positioned in a single plane, or substantially in the same plane.

Surgical retractor 800 also includes lighting elements 891 and 893. Lighting element 891 is connected to joint 805, or may be connected to a leg near joint 805 (e.g., leg 843). Lighting element 893 is connected to joint 808 or may be connected to a leg near joint 808 (e.g., leg 841). Lighting elements 891, 893 may be any suitable light source, such as a light-emitting diode (LED) light source. Other types of light sources may be used.

In one embodiment, the light elements are attached to the legs of the retractor and are movable. The lighting elements are adapted to slide up and down the legs between the joints and be fixed in place with a locking mechanism. The lighting elements can be removed. The lighting elements are wireless. The lighting elements may be LED or conventional light sources or another type of light source. The lighting elements each have independent on/off switches. The lighting elements are disposable. A surgeon may choose where and how many lighting elements to attach to various legs for each case. Each lighting element has a toggle on/off button and therefore may be switched during surgery as needed.

In the expanded state, manipulator arms 875, 877 define a first plane, rectangular structure 854 defines a second plane different from the first plane, and trapezoidal structure 856 defines a third plane different from the first and second planes. An internal three-dimensional volume defined by and bounded by the first, second and third planes is created.

Figure 8B:
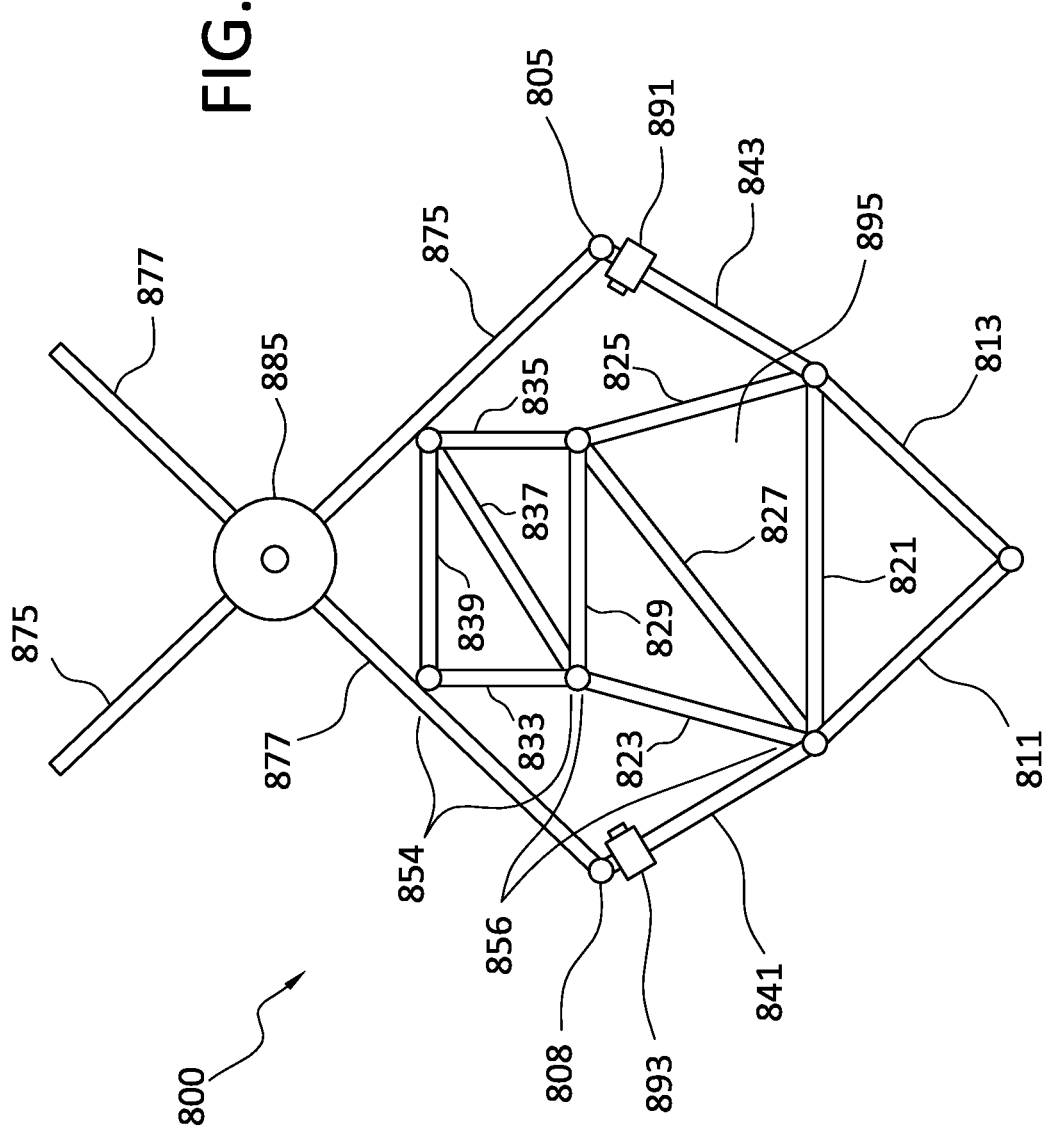
FIG. 8B shows the retractor device of FIG. 8A in an expanded state.

FIG. 8B shows the retractor of FIG. 8A in an expanded state in accordance with an embodiment. When in its expanded state, manipulator arms 875, 877, rectangular structure 854, trapezoidal structure 856, and legs 841 and 843 form a three-dimensional box-like structure that creates an internal three-dimensional volume 895 between, and bounded by, the legs and manipulator arms.

Lighting elements 891, 893 illuminate the internal three-dimensional volume 895 created by retractor 800 when retractor 800 is in its expanded state.

In other embodiments, retractor 800 may include more than two lighting elements. For example, retractor 800 may include a lighting element at each joint.

Figure 9:
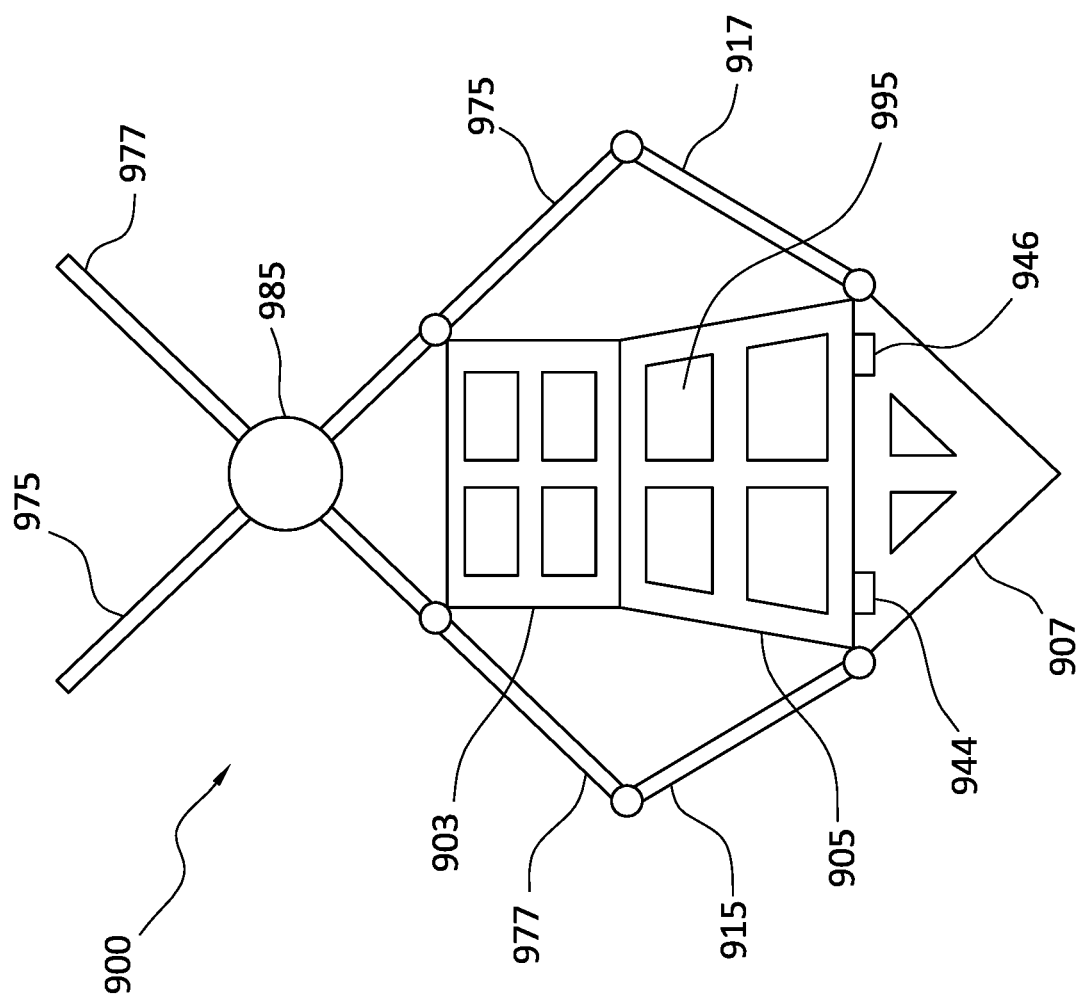
FIG. 9 shows a retractor device in accordance with another embodiment.

FIG. 9 shows a surgical retractor in accordance with another embodiment. Retractor 900 includes legs 915 and 917, and a plurality of panels 903, 905, and 907. Retractor 900 also includes manipulator arms 975, 977, which may be manipulated to cause retractor 900 to expand and contract between a non-expanded state and an expanded state in a manner similar to that described above with respect to retractor 700. Retractor 900 has a non-expanded (flattened) state and an expanded state, similar to retractor 700 of FIGS. 7A-7C. In its expanded state, the legs 915, 917, arms 975, 977, and panels 903, 905, and 907 of retractor 900 create an internal three-dimensional volume 995 between, and bounded by, the legs, arms, and panels.

In the embodiment of FIG. 9, retractor 900 also includes lighting elements 944 and 946. Lighting elements 944, 946 are disposed on panel 907. Lighting elements 944, 946 illuminate the internal three-dimensional volume 995 created by the retractor in its expanded state. Retractor 900 may include more than two lighting elements. For example, retractor 900 may include a lighting element at one or more of the joints, or at every joint. Lighting elements may be disposed on other panels, on one or more legs or on one or more arms.

Thus, in accordance with an embodiment, a surgical retractor device includes a structure having a plurality of legs and a plurality of joints, each leg being connected to at least one second leg at a joint, wherein the structure has a non-expanded position in which the structure does not form an internal three-dimensional volume and an expanded position in which the structure forms a three dimensional structure having an internal three-dimensional volume. The retractor also includes first and second manipulator arms, each of the first and second manipulator arms connected to at least two joints of the structure, the manipulator arms adapted to be manipulated by a hand of a user. The retractor further includes a connector adapted to hold the first and second manipulator arms in a crossed position, defining a point of intersection of the first and second manipulator arms. The connector holds the first and second manipulator arms at the point of intersection. The connector is adapted to allow the first and second manipulator arms to move to cause an angle formed by the first and second manipulator arms to change in response to pressure provided by the hand of the user. Movement of the first and second manipulator arms causes the structure to move between the non-expanded position and the expanded position.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A surgical retractor device comprising:
   a structure comprising a plurality of legs and a plurality of joints, each joint comprising an intersection of a first leg and a second leg, wherein the structure has a non-expanded state in which the structure does not form an internal three-dimensional volume and an expanded state in which the structure forms a three dimensional structure having an internal three-dimensional volume; and
   first and second manipulator arms, each of the first and second manipulator arms connected to at least two joints of the structure, the manipulator arms adapted to be manipulated by an external entity;
   wherein the first and second manipulator arms are adapted to be placed in a crossed position, defining an angle between the first and second manipulator arms, the first and second manipulator arms being further adapted to move to cause the angle to change in response to pressure provided by the external entity;
   wherein movement of the first and second manipulator arms causes the structure to move between the non-expanded state and the expanded state.

2. The surgical retractor of claim 1, wherein the external entity is a hand of a user.

3. The surgical retractor device of claim 1, wherein the legs comprise one of: plastic, ceramic, and metal.

4. The surgical retractor device of claim 1, further comprising:
   a plurality of lighting elements, each lighting element being connected to a selected one of the plurality of legs.

5. The surgical retractor device of claim 4, wherein each lighting element comprises a light emitting diode (LED) light source.

6. The surgical retractor device of claim 1, wherein the plurality of legs form a rectangular structure and a trapezoidal structure.

7. The surgical retractor device of claim 6, wherein:
   the first and second manipulator arms, the rectangular structure, and the trapezoidal structure are positioned in the same plane, when the structure is in the non-expanded state; and
   the first and second manipulator arms define a first plane, the rectangular structure defines a second plane different from the first plane, and the trapezoidal structure defines a third plane different from the first and second planes, when the structure is in the expanded state.

8. The surgical retractor device of claim 7, wherein the first, second, and third planes define an internal three-dimensional volume, when the structure is in the expanded state.

9. The surgical retractor device of claim 1, further comprising:
a connector adapted to hold the first and second manipulator arms in the crossed position, defining a point of intersection of the first and second manipulator arms, the connector being connected to the first and second manipulator arms at the point of intersection.

10. The surgical retractor device of claim 9, wherein the connector includes:
a first disk comprising a channel adapted to hold the first manipulator arm; and
a second disk is adapted to hold the second manipulator arm, the second disk being connected to the first disk;
wherein the first and second disks are adapted to rotate relative to each other.

11. The surgical retractor of claim 10, wherein the connector further includes a locking button having a locked position and an unlocked position, the locking button being adapted to lock the first disk in a position relative to the second disk, wherein the first and second disks can rotate relative to each other when the locking button is in the unlocked position, wherein the first and second disks cannot rotate relative to each other when the locking button is in the locked position.

12. The surgical retractor of claim 1, wherein each of the joints includes one of: a ball joint and a swivel.

* * * * *